(12) United States Patent
Glover

(10) Patent No.: US 10,932,880 B2
(45) Date of Patent: Mar. 2, 2021

(54) MEDICAL DEVICE FIXATION APPARATUS

(71) Applicant: Benedict Glover, Toronto (CA)

(72) Inventor: Benedict Glover, Toronto (CA)

(*) Notice: Subject to any disclaimer, the term of this patent is extended or adjusted under 35 U.S.C. 154(b) by 0 days.

(21) Appl. No.: 16/405,478

(22) Filed: May 7, 2019

(65) Prior Publication Data

US 2019/0336234 A1    Nov. 7, 2019

Related U.S. Application Data

(60) Provisional application No. 62/667,672, filed on May 7, 2018.

(51) Int. Cl.
| | | |
|---|---|---|
| *A47B 91/00* | (2006.01) | |
| *A61B 50/20* | (2016.01) | |
| *A61M 25/02* | (2006.01) | |
| *F16M 13/02* | (2006.01) | |
| *A61B 50/00* | (2016.01) | |

(52) U.S. Cl.
CPC ............ *A61B 50/20* (2016.02); *A61M 25/02* (2013.01); *F16M 13/022* (2013.01); *A61B 2050/002* (2016.02); *A61B 2050/21* (2016.02); *A61M 2025/026* (2013.01); *A61M 2025/0266* (2013.01)

(58) Field of Classification Search
CPC ....... A61B 50/20; F16M 11/22; F16M 13/022
See application file for complete search history.

(56) References Cited

U.S. PATENT DOCUMENTS

| | | | | |
|---|---|---|---|---|
| 3,918,446 A | * | 11/1975 | Buttaravoli | A61M 25/02 604/180 |
| 5,181,609 A | * | 1/1993 | Spielmann | A61B 50/362 206/366 |
| 5,202,098 A | * | 4/1993 | Nichols | A61L 2/26 206/363 |
| 5,363,862 A | * | 11/1994 | Mercier | A61B 50/3001 128/846 |
| 5,490,975 A | * | 2/1996 | Dane | A61L 2/26 206/379 |
| 7,965,185 B2 | * | 6/2011 | Cambre | G09B 23/28 340/572.1 |
| 8,915,363 B2 | * | 12/2014 | Hawkes | A61C 19/02 206/370 |
| 9,994,381 B2 | * | 6/2018 | Sweeney | B32B 27/10 |
| 2007/0253864 A1 | * | 11/2007 | Maguire, Jr. | A61L 2/206 422/28 |
| 2010/0008882 A1 | * | 1/2010 | LaVay | A61K 8/891 424/70.12 |

* cited by examiner

*Primary Examiner* — Amy J. Sterling
(74) *Attorney, Agent, or Firm* — Bereskin & Parr LLP/S.E.N.C.R.L, S.R.L.

(57) ABSTRACT

An apparatus for fixing a device in a selected position comprises a base having a deformable adherent material disposed thereon, and at least one stability feature associated with the base that allows the apparatus to be maintained in a location and position. The deformable adherent material substantially conforms to at least a portion of a shape of the device and removably fixes the device in the selected position. Although not limited thereto, the apparatus is useful in surgical and interventional procedures for quickly and reliably fixing a medical device such as a catheter at a selected position and orientation while allowing easy removing and repositioning of the device.

18 Claims, 3 Drawing Sheets

MEDICAL DEVICE FIXATION APPARATUS

RELATED APPLICATION

This application claims the benefit of the filing date of Application No. 62/667,672, filed on 7 May 2018, the contents of which are incorporated herein in their entirety.

FIELD

This invention relates to surgical interventional apparatus. More specifically, this invention relates to an apparatus for securing a medical device during surgical and interventional procedures.

BACKGROUND

Many surgical and interventional procedures employ catheters to introduce energy (radiofrequency, microwave, cryo-energy), fluids, contrast agents, medications, or instruments into a patient. It may be necessary to secure a catheter in position for an extended period of time during the procedure, to maintain the catheter in a desired position and orientation. This allows the surgeon/operator to perform other tasks and manipulate other catheters during the procedure. Typically this is achieved using adhesive tape or dressing such as Tegaderm™ (3M, St. Paul, Minn., U.S.A.). However, the use of an adhesive tape or the like to secure the catheter has many drawbacks. For example, the catheter can move while the tape is applied, and repositioning of the catheter, as may be required, is difficult as it is secured with the tape which is then difficult to remove and re-apply.

Cardiac mapping and catheter ablation are examples of procedures where catheter positioning and stability are critical. These procedures are used to treat arrhythmias (irregular heartbeat caused by problems with electrical signals within the heart) which may result in significant symptoms such as palpitations, shortness of breath, fatigue and reduced exercise tolerance. In order to perform these procedures wire catheters are used to record electrical information. For example, a catheter may be introduced into the femoral vein (at the top of the leg) through the vena cava and into various chambers of the heart. In this minimally invasive procedure the wires are positioned from outside the patient's body by pushing and rotating the catheters while they are visualized using imaging such as fluoroscopy and an electroanatomic map. The electroanatomic map is a positioning system in which the wires can be visualized within the heart using either magnetic data, impedance data, or most commonly a combination of both. This allows reconstruction of the anatomy and the electrical data within the heart which is useful for management of the arrhythmia.

In order to create an electroanatomic map a stable reference point is required. This is generally a catheter within the coronary sinus (the main vein within the heart) and all of the anatomic points which are visualized are relative to this catheter. However, if this catheter is displaced the map shifts by the equivalent distance in which the catheter has moved. It is therefore critical that this catheter does not move. As soon as this catheter is positioned within the coronary sinus it is released by the operator and other catheters are positioned. The catheter handle may be left freely on the drape over the patient with the assumption that it will not move. Alternatively, the catheter or handle may be fixed to the drape using an adhesive dressing. However, neither of these options is satisfactory since the catheter can move if left free, resulting in a map shift, and if secured using adhesive dressing it cannot be easily repositioned if required. Additionally, other catheters which are positioned within the heart often require the operator to maintain manual control so that they do not dislodge. This is often difficult as there may be only one operator who has to position other catheters or move to another location within the procedural suite and therefore conventionally cannot take their hands off the catheter.

SUMMARY

One aspect of the invention relates to an apparatus for fixing a device in a selected position; comprising: a base having a top surface and a bottom surface; a deformable adherent material disposed on the top surface of the base; at least one stability feature associated with the base that maintains the apparatus in a location and position; wherein the deformable adherent material substantially conforms to at least a portion of a shape of the device placed thereon; wherein the deformable adherent material removably fixes the device thereon in the selected position.

In one embodiment, the deformable adherent material is a silicon-based organic polymer.

The at least one stability feature may allow the apparatus to be attached to an object. The at least one stability feature may be at least one fastener selected from adhesive, tape including double-sided tape, hook and loop fastener, clip, and magnet. In one embodiment, the at least one stability feature comprises an adhesive strip or double-sided tape. In one embodiment, the at least one stability feature comprises one or more clips.

In one embodiment, the base of the apparatus is rigid. In another embodiment, the base of the apparatus is flexible.

The apparatus may be used with a medical device. The device may be at least one of a catheter and a catheter handle. The apparatus may be sterilizable.

Another aspect of the invention relates to a method for fixing a device in a selected position; comprising: disposing a deformable adherent material on a base; using at least one stability feature associated with the base to maintain the base in a location and position; placing the device on the deformable adherent material; wherein the deformable adherent material substantially conforms to at least a portion of a shape of the device placed thereon; wherein the deformable adherent material removably fixes the device thereon in the selected position.

According to certain embodiments of the method, the device may be a medical device. In one embodiment the device is at least one of a catheter and a catheter handle. The method may comprise sterilizing an apparatus comprising the deformable adherent material, the base, and the at least one stability feature.

BRIEF DESCRIPTION OF THE DRAWINGS

For a greater understanding of the invention, and to show more clearly how it may be carried into effect, embodiments will be described, by way of example, with reference to the accompanying drawings, wherein.

DETAILED DESCRIPTION OF EMBODIMENTS

Figure 1A:
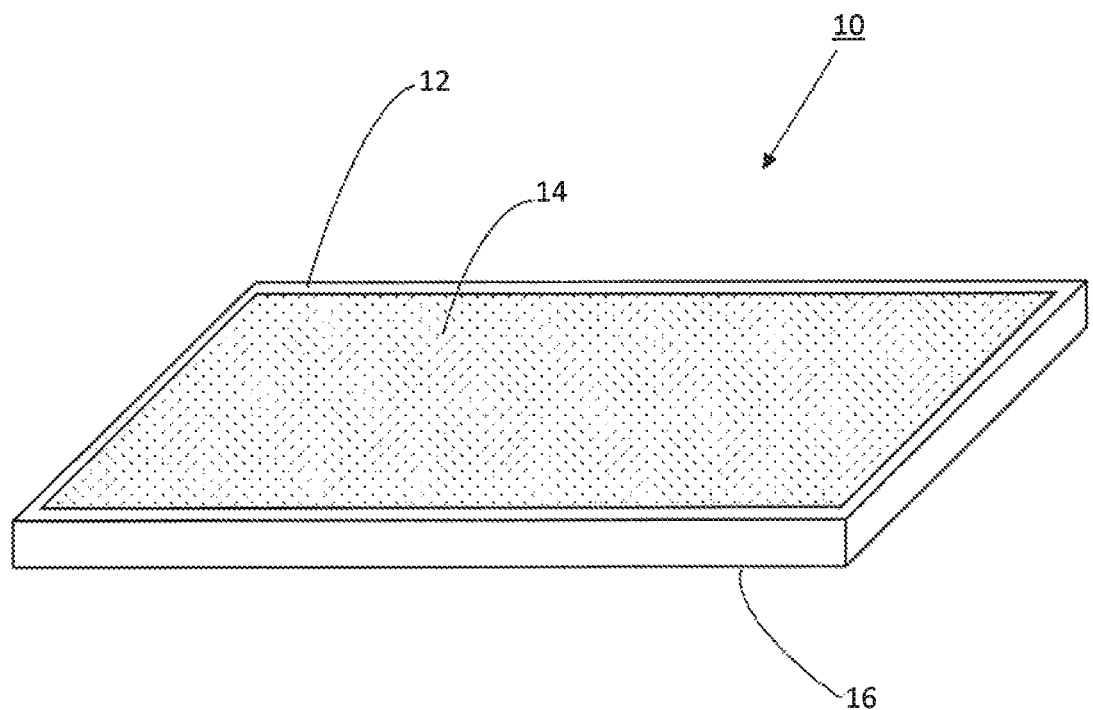
FIG. 1A is a drawing of an apparatus according to an embodiment of the invention.
Figure 1B:
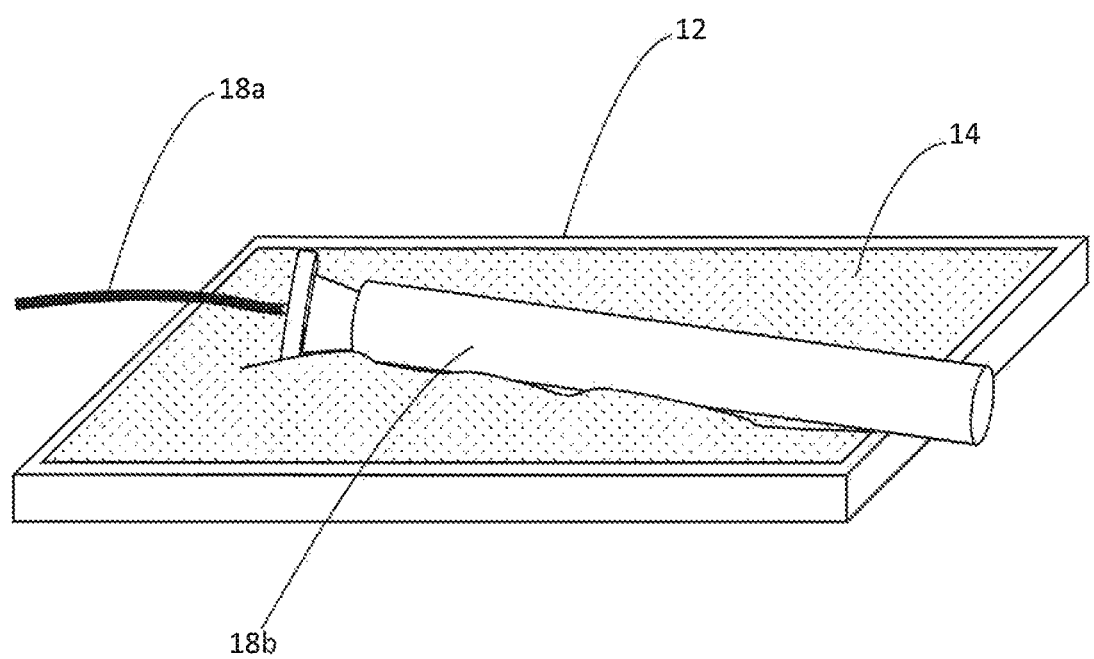
FIG. 1B is a drawing of the embodiment of FIG. 1A, with a medical device.

Described herein is an apparatus for fixing a medical device such as a catheter in a selected position. FIG. 1A is a representative drawing of an embodiment. Referring to FIG. 1A, the apparatus 10 includes as one feature a deformable adherent material 14 that adheres to a medical device placed thereon, substantially fixing the medical device in the position and orientation in which it is initially placed such that the need for any adjustment is minimized or eliminated. However, should adjustment of the device position or orientation be required, the device can easily be removed and repositioned/reoriented. The apparatus avoids any requirement for additional connections or attachments to the device to achieve reliable and secure fixation once it is placed on the deformable adherent material. FIG. 1B is a representative drawing of the embodiment of FIG. 1A, with a medical device, in this example a catheter 18a and catheter handle 18b, fixed thereto.

The deformable adherent material 14 may be disposed on a base 12, as described below, as a substantially continuous layer as shown in FIG. 1A. Alternatively, the deformable adherent material may be disposed in patches such as strips or pads, or the like, suitably arranged. The material is disposed at a thickness or depth that allows the medical device to "sink" somewhat therein when the device is placed with minimal force. This is shown diagrammatically in FIG. 1B. In some embodiments the thickness of the deformable adherent material may be about, e.g., 1 mm to 10 mm, or 2 to 5 mm, although other thicknesses may be used. Thus, the deformable adherent material has suitable properties of viscosity, hardness, and elasticity that allow the material to deform and conform to surfaces of the medical device with which it is in contact. The deformable adherent material also has a suitable tackiness that provides instant "grab" of the medical device upon contact. The amount of grab, i.e., the degree to which the medical device is captured or fixed in the deformable adherent material, may be controlled by the amount of force applied when placing the medical device thereon. For example, applying greater force causes the medical device to sink deeper into the deformable adherent material, resulting in more surface area of the device in contact with the deformable adherent material, and greater grab. This advantageously allows the surgeon or operator to control the degree to which a device is secured. For example, the device may be placed lightly upon the deformable adherent material, fixing it in an initial position and orientation while the surgeon/operator verifies that the correct/desired position and orientation has been reached. Once verified, the surgeon/operator need only apply further force to the device to strengthen its fixation in the deformable adherent material, substantially without altering the position and orientation of the device.

However, even when considerable force is applied, the medical device can be removed and/or repositioned/reoriented in the deformable adherent material. Further, upon removing the medical device, substantially no residual deformable adherent material or tackiness is left on the medical device. The tackiness of the deformable adherent material may persist at a level sufficient to securely fix the medical device for a duration of at least several hours, i.e., long enough for many surgical interventions, and typically for as long as 24 hours. It will be appreciated that the apparatus may be provided in a sealed sterile package and therefore the tackiness persists for such duration after breaking the seal.

The deformable adherent material may be a gel. Suitable gel materials are known in the art, such as silicon-based organic polymers, e.g., organopolysiloxanes. The gel may be reinforced with one or more additive and/or filler to achieve desired characteristics of viscosity, hardness, elasticity, and tackiness. Examples include, but are not limited to, titanium dioxide, calcium carbonate, lithopone, zinc oxide, zirconium silicate, silica aerogel, iron oxide, diatomaceous earth, silazane-treated silica, precipitated silica, fumed silica, mined silica, glass fibers, magnesium oxide, chromic oxide, zirconium oxide, aluminum oxide, alpha quartz, and calcined clay, as known in the art.

As described above, apparatus 10 includes a base 12 that supports and/or contains the deformable adherent material 14. In one embodiment the base may be rigid so as to resist bending when a force is applied thereto. For example, the base may have sufficient rigidity to resist bending when a force associated with placing the medical device in the deformable adherent material. In another embodiment the base may be somewhat rigid but also flexible enough to at least partially conform with the shape of the object or material that it is placed upon but also to resist excessive bending when a force is applied thereto. In another embodiment the base may be flexible, allowing it to bend so as to conform to the shape of an object upon with the apparatus is placed. The base, and hence the area of the deformable adherent material available, may be sized according to the number and/or size of devices to be fixed thereto. That is, some surgical interventions may require a larger size to accommodate a plurality of devices. Alternatively, it may be preferable to use two or more smaller-sized apparatus to accommodate multiple devices.

In use, the surgeon/operator places the apparatus in a desired location and position so that one or more medical devices may then be fixed thereto. Thus, it is important that the apparatus does not move from its location and position, since any movement will affect the position and/or orientation of the one or more medical devices fixed thereto. In some instances, it may be possible to locate the apparatus against nearby objects, or, e.g., against a limb/torso of a patient, so that the apparatus does not move. In some embodiment, the apparatus may have substantial mass, thereby contributing to its stability. However, to ensure that the apparatus does not move, embodiments may be provided with one or more stability feature that maintains it in a desired location and position. In particular, the base 12 has a bottom surface 16 which may accommodate one or more such stability features. In one embodiment, such a stability feature may be a soft polymeric or rubber "grip" material that provides significant grip (i.e., opposes sliding) on an object on which it is placed. The grip material may have a rough or textured surface that enhances such grip. The grip material may be disposed on the bottom surface 16 either as a substantially continuous layer, or as a series of patches, strips, etc. In another embodiment, such stability feature allows the apparatus 10 to be fixed or attached to an object. In some embodiments the base also has side surfaces which may optionally or alternatively accommodate such a stability feature. There are many ways that a stability feature may be implemented. For example, one or more fastener including, but not limited to, adhesive, tape including double-sided tape, hook and loop fastener, clip, and magnet, may be provided. In a surgical setting the apparatus may be placed on the drape covering the patient, and the fastener used to secure the apparatus to the drape. An embodiment for such a setting may include as a fastener an adhesive strip or double-sided tape having its outer adhesive surface covered by a removable protective film. The surgeon or clinician simply peels away the protective film, and applies the apparatus to the drape at the desired location. In another embodiment, one or more clips, such as "alligator" clips, are disposed at one or more sides of the base. The one or more clips allow the apparatus to be clipped to the drape, or to a nearby object.

It will be appreciated that the apparatus will be useful in various applications other than medical/surgical and interventional procedures. Accordingly, the apparatus is not limited to medical/surgical and interventional procedures. However, for such applications, the apparatus may be prepared in a sterile environment, and/or the complete apparatus, including the deformable adherent material, is capable of being sterilized for use in the operating room.

Embodiments will be further described by way of the following non-limiting Example.

Example

Figure 2:
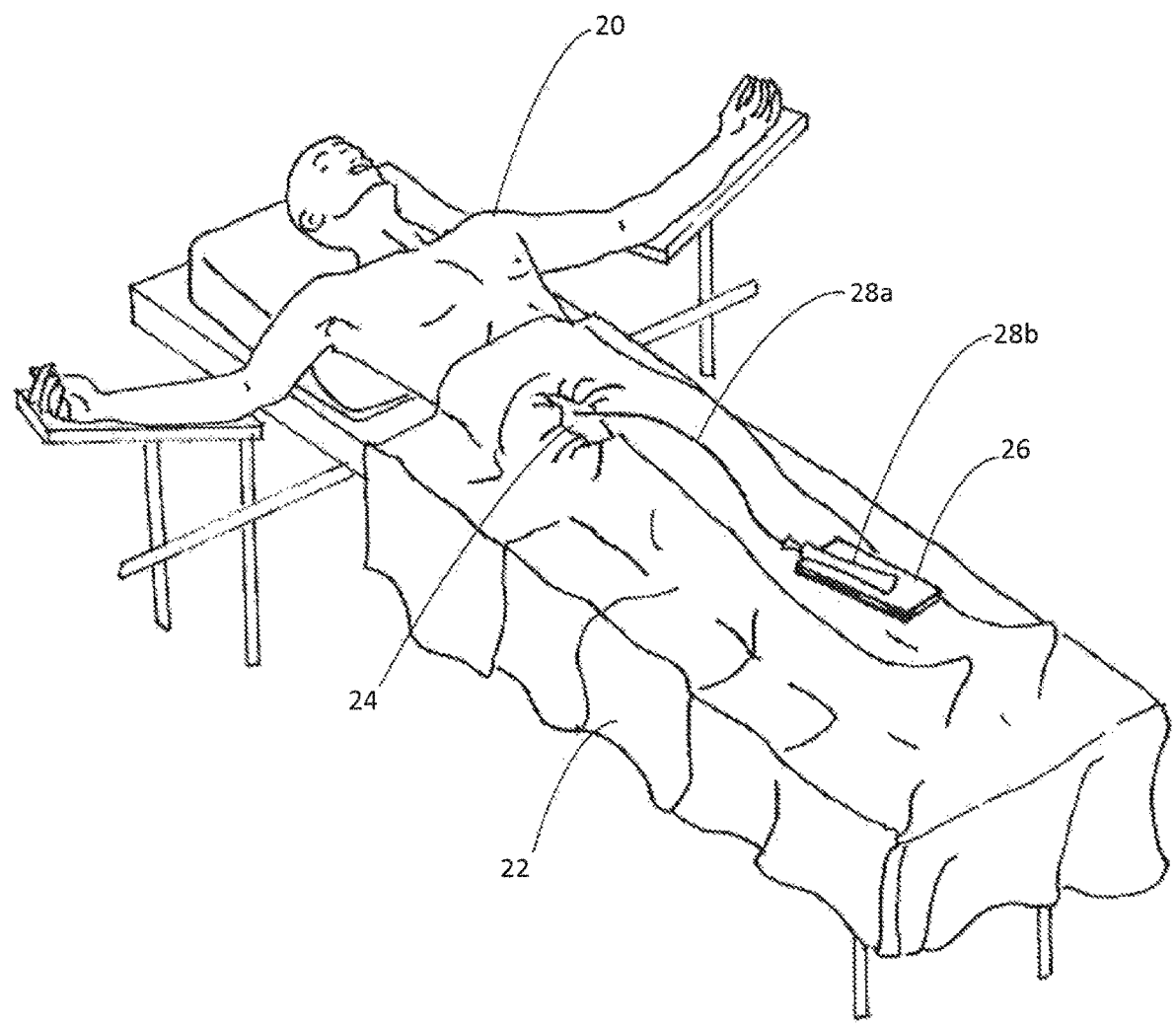
FIG. 2 is a drawing showing an embodiment being used in a surgical interventional procedure.

An embodiment of the apparatus as used in surgical procedures such as cardiac mapping and catheter ablation is shown in FIG. 2. As noted above, these are procedures where catheter positioning and stability are critical. The embodiment provides a stable platform to prevent significant movement of the catheters within the heart in order to ensure that a stable map can be created, and that electrograms can be recorded while allowing the operator to remove their hands from the catheter. The patient 20 is covered with a drape 22 and an opening 24 in the drape provides access to the patient's right upper leg. The apparatus 26 according to this embodiment has a base with an adhesive bottom surface which is adhered to the drape 22 over the patient. A layer of deformable adherent material is disposed on the upper surface of the base. When the catheter 28a is deemed to be in a stable desirable location it is placed in the deformable adherent material. FIG. 2 shows the catheter handle 28b placed in the deformable adherent material, where it is fixed in a position and orientation as deemed appropriate by the operator. The deformable adherent material conforms to and adheres to the portion of the catheter handle 28b, and therefore the catheter will be maintained in this fixed position while the operator continues to perform the procedure. That is, the catheter may then be left in this position, freeing the operator's hands to attend to other tasks. Thus, relative to prior approaches using adhesive tape or dressing to secure the catheter, the apparatus according to this embodiment substantially improves the stability of the cardiac map and also allows the operator to position catheters in selected locations and perform other tasks at the same time, since the catheter is reliably fixed in the desired position and orientation.

All cited publications are incorporated herein by reference in their entirety.

EQUIVALENTS

While the invention has been described with respect to illustrative embodiments thereof; it will be understood that various changes may be made to the embodiments without departing from the scope of the invention. Accordingly, the described embodiments are to be considered merely exemplary and the invention is not to be limited thereby.

The invention claimed is:

1. Apparatus for fixing a medical device in a selected position during a medical procedure, the apparatus comprising:
   a base having a top surface and a bottom surface;
   a deformable adherent material comprising a non-fluid gel material disposed on the top surface of the base;
   at least one stability feature associated with the base;
   wherein the deformable adherent material substantially conforms to at least a portion of a shape of the medical device placed thereon;
   wherein the deformable adherent material removably fixes the medical device thereon in the selected position.

2. The apparatus of claim 1, wherein the deformable adherent material is a silicone-based organic polymer.

3. The apparatus of claim 1, wherein the at least one stability feature allows the apparatus to be attached to an object.

4. The apparatus of claim 1, wherein the at least one stability feature is at least one fastener selected from adhesive, tape, hook and loop fastener, clip, and magnet.

5. The apparatus of claim 1, wherein the at least one stability feature comprises an adhesive strip or double-sided tape.

6. The apparatus of claim 1, wherein the base is rigid.

7. The apparatus of claim 1, wherein the base is flexible.

8. The apparatus of claim 1, wherein the medical device is at least one of a catheter and a catheter handle.

9. The apparatus of claim 1, wherein the apparatus is sterilizable.

10. The apparatus of claim 1, wherein the deformable adherent material is of a thickness between 1 mm and 10 mm.

11. The apparatus of claim 10, wherein the deformable adherent material is of a thickness between 2 mm and 5 mm.

12. The apparatus of claim 8, wherein the base and the deformable adherent material are sized to receive at least one of the catheter or the catheter handle.

13. The apparatus of claim 2, wherein the deformable adherent material is reinforced with an additive material comprising at least one selected from the group of titanium dioxide, calcium carbonate, lithopone, zinc oxide, zirconium silicate, silica aerogel, iron oxide, diatomaceous earth, silazane-treated silica, precipitated silica, filmed silica, mined silica, glass fibers, magnesium oxide, chromic oxide, zirconium oxide, aluminum oxide, alpha quartz, and calcined clay.

14. The apparatus of claim 1, wherein the apparatus is reusable.

15. The apparatus of claim 1, wherein the deformable adherent material removably fixes the medical device by exerting an adhering force on the medical device that is a function of an application force of the medical device when it is placed on the deformable adherent material.

16. The apparatus of claim 1, wherein the deformable adherent material is disposed on the base as a continuous layer.

17. The apparatus of claim 1, wherein the deformable adherent material is disposed on the base in patches.

18. The apparatus of claim 1, wherein the base further comprises;
   a first edge, a second edge, a third edge and a fourth edge;
   a first wall extending transversely from the first edge;
   a second wall extending transversely from the second edge;
   a third wall extending transversely from the third edge;
   a fourth wall extending transversely from the fourth edge;
   wherein the deformable adherent material is disposed on the top surface of the base and confined by the first wall, the second wall, the third wall and the fourth wall;
   wherein the deformable adherent material is of a thickness equivalent to the height of the adjoining walls.

* * * * *

UNITED STATES PATENT AND TRADEMARK OFFICE
CERTIFICATE OF CORRECTION

| | | |
|---|---|---|
| PATENT NO. | : 10,932,880 B2 | Page 1 of 1 |
| APPLICATION NO. | : 16/405478 | |
| DATED | : March 2, 2021 | |
| INVENTOR(S) | : Benedict Glover | |

It is certified that error appears in the above-identified patent and that said Letters Patent is hereby corrected as shown below:

In the Claims

Column 6, Line 14, Claim 4 "hook and loop fastener, clip, and magnet." should read -- hook and loop fastener, and magnet. --.

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*